United States Patent [19]
Brunner et al.

[11] 4,261,828
[45] Apr. 14, 1981

[54] APPARATUS FOR THE DETOXIFICATION OF BLOOD

[75] Inventors: Gorig Brunner, Hanover; Christopher-John Holloway, Sibbesse; Wilfried Schäl, Bad Homburg, all of Fed. Rep. of Germany

[73] Assignee: Dr. Edward Fresenius Chemisch-pharmazeutische Industrie KG. Apparatebau KG, Bad Homburg, Fed. Rep. of Germany

[21] Appl. No.: 73,240

[22] Filed: Sep. 7, 1979

[30] Foreign Application Priority Data

Sep. 19, 1978 [DE] Fed. Rep. of Germany ....... 2840655

[51] Int. Cl.$^3$ .............................................. B01J 8/02
[52] U.S. Cl. .................................. 210/287; 210/290; 210/927; 422/44; 435/182; 435/288
[58] Field of Search ............... 128/214 R; 210/24, 36, 210/40, 282, 287, 290, 502, 504, 506, 510, DIG. 23, 663, 668, 927; 252/428; 435/174–182, 288; 422/44

[56] References Cited

U.S. PATENT DOCUMENTS

| | | | |
|---|---|---|---|
| 2,682,268 | 6/1954 | Ryan et al. | 210/24 |
| 3,420,709 | 1/1969 | Barrett et al. | 210/36 |
| 3,442,819 | 5/1969 | Herbert | 252/428 |
| 3,808,124 | 4/1974 | Dziobkowski et al. | 210/36 |
| 4,048,018 | 9/1977 | Coughlin | 435/288 |
| 4,131,544 | 12/1978 | Elahi | 210/502 |
| 4,190,542 | 2/1980 | Hodgson et al. | 210/282 |

*Primary Examiner*—Ivars C. Cintins
*Attorney, Agent, or Firm*—W. G. Fasse; D. F. Gould

[57] ABSTRACT

A blood detoxification apparatus comprises a housing filled with a plurality of substantially spherical reaction bodies. Each reaction body comprises an embedding material and active ingredient particles such as adsorbents and/or enzymes embedded in the embedding material which is blood compatible but nonpermeable for corpuscular blood components. The active ingredients may have a dust or powder or granular consistency but are substantially smaller in diameter than the reaction bodies which may be distributed in layers in said housing whereby the active ingredients in different layers may be different.

12 Claims, 2 Drawing Figures

APPARATUS FOR THE DETOXIFICATION OF BLOOD

BACKGROUND OF THE INVENTION

The invention relates to an apparatus for the detoxification of blood by means of adsorbents and/or carrier bound enzymes in accordance with the method of the so-called hemoperfusion. In this method the blood is conducted in an artificially produced, extracorporeal circuit through a capsule or column which is filled, for example, with adsorption means. A survey regarding the relevant prior art may be found in the book "Entgiftung mit Haemoperfusion" (Detoxificaton By Means Of Hemoperfusion), published by Carl Bindernagel, Friedberg/Hessen, 1977 or in the work "Hemoperfusion Over Ion-Exchange Resins and Polymeric Adsorbents", International Journal of Artificial Organs, Volume 1, Number 196, 1978.

Different problems occur in the prior art devices for the blood detoxification according to the hemoperfusion method. These problems cannot be solved simultaneously in an optimal manner due to the requirements being incompatible or to some extent seemingly incompatible. It is of special importance in this connection that the adsorbents which come into consideration, for example, active charcoal or certain synthetic resins as well as certain carrier bound enzymes have a strongly impairing effect on the corpuscular blood components upon direct contact therewith, especially causing a high loss of thromocytes. In order to avoid this effect as much as possible, the particles of adsorption means are frequently provided with a coating, for example, of cellulose derivatives partially in combination with albumins. The coating should have a high permeability for the substances to be adsorbed, however, at the same time they prevent the direct contact between the corpuscular blood components and the adsorbents. For this purpose hollow fibers made of cellulose derivatives are also used which are filled with an adsorbtion means while the blood contacts the outside of the hollow fibers.

OBJECTS OF THE INVENTION

In order to minimize any damage to the blood while simultaneously achieving an optimal effect with regard to the materials in solution in the blood the following requirements, among others, should be simultaneously satisfied. These requirements apply in the same sense also for carrier bound enzymes:

(1) there should be no direct contact between the corpuscular blood components and the adsorption means;

(2) the total contact surface between the blood with the blood corpuscules therein and the adsorption bodies should be as small as possible whereby adsorption bodies are to be understood to be, for example, active charcoal particles provided with a semipermeable coating;

(3) the nonpermeability of the protective coating must be only effective for the corpuscular blood components while providing a permeability for all substances in solution up to micro-molecules to thereby provide a molecular sieve;

(4) to provide a large total contact surface for the transition of the substances in solution into the adsorption means having regard to a high adsorption speed.

SUMMARY OF THE INVENTION

The invention makes it possible to satisfy these conditions very substantially simultaneously contrary to prior art devices. This is accomplished substantially in that small particles of an adsorption means or enzyme carrier or a combination of adsorption means and enzyme carriers are embedded in a highly permeable, blood compatible base material in order to form thereof larger particles, for example, balls, which have a relatively small outer surface in relation to their volume and to the reaction capacity contained therein, said outer surface coming in contact with the blood. In this connection advantage is taken of the fact that the surface of a body having, for example, a spherical shape, increases with the square of the diameter, whereas the volume increases with the cubic power. Due to the large permeability of the base material, the substances in solution in the blood have a quasi-free access to the relative small particles of the adsorption means or enzyme carriers embedded in the base material. Thus, the substances can be quickly adsorbed or brought to a reaction. Besides, the small grain size of the adsorption means results in an especially high utilization of the available adsorption capacity. Contrary thereto, and as is known, the available adsorption capacity remains partially unused in adsorption means of coarse grain size because the access to the innermost regions is made more difficult from the start or is partially blocked by adsorption processes.

The invention provides that the bodies containing the adsorption means and/or the immobilized enzymes, are shaped to have a uniform configuration, preferably a spherical shape. This feature has the advantage relative to comparable prior art arrangements including irregularly shaped particles, that the adsorption bodies in a capsule or column into which they are eventually filled assume a substantially uniform geometrical distribution and hence a defined flow distribution. This is of substantial importance with regard to the possibility of blood coagulation in stagnation zones as well as with regard to a utilization of the reaction capacity which should be as uniform as possible.

BRIEF FIGURE DESCRIPTION

Details and further characteristics of the invention result from the following description taken in combination with the drawings, wherein.

DETAILED DESCRIPTION OF PREFERRED EXAMPLE EMBODIMENTS AND OF THE BEST MODE OF THE INVENTION

Figure 1:
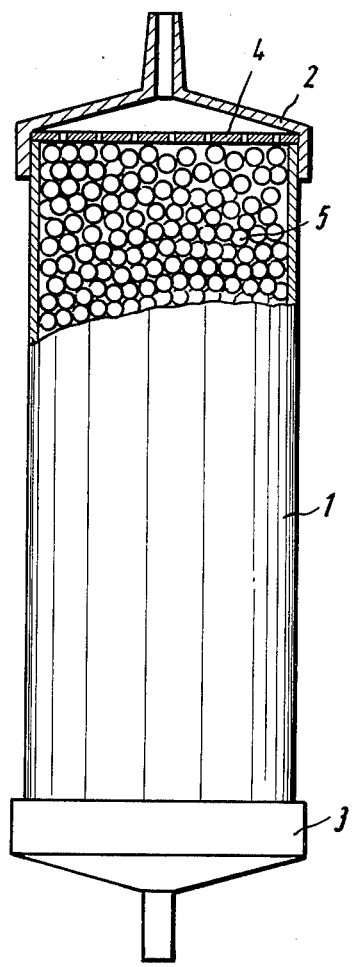
FIG. 1 shows an adsorption or reaction column according to the invention.

In the example embodiment shown in FIG. 1, the adsorption or reaction column is composed substantially of a tube 1 and two connecting caps 2 and 3, whereby the latter are provided with connecting nipples for the supply and removal of the blood. Screen plates 4 are inserted into the connecting cap which keep the adsorption or reaction bodies 5, filled into the column, away from the inlet and outlet openings. The parts 1, 2, 3, and 4 are made of blood compatible synthetic materials and are interconnected by conventional techniques. Other configurations for the capsule or columns may naturally be used and such configurations may be known in the art or obvious to the person skilled in the art.

According to a special embodiment of the invention the column is subdivided by additional screen plates into two or more sections as viewed in the longitudinal direction and different types of adsorption and/or reaction bodies 5 are located in these sections. This feature provides the possibility to combine one or several enzymatic reactions with adsorptions in a timed sequence corresponding to the passage of the blood through the different sections or layers of the column. An example of use is the enzymatic decomposition of urea by means of reaction bodies which contain the enzyme urease in an immobilized form followed by an adsorption of the ammonia ions formed thereby in a suitable ion exchanger.

Another embodiment of the invention provides that the capsule or column is filled with a mixture of different types of adsorption and/or reaction bodies in order to combine enzymatic reactions and/or adsorptions. Also, the reaction bodies may comprise certain substances or a mixture of substances which have different therapeutic effects.

Figure 2:
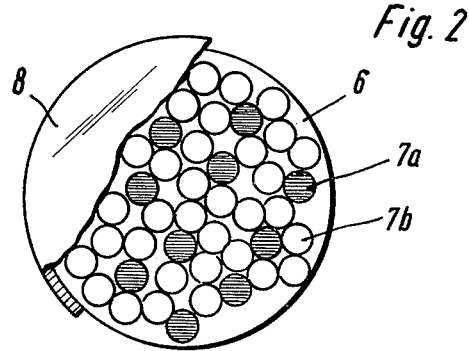
FIG. 2 illustrates an individual adsorption or reaction body.

FIG. 2 illustrates a single adsorption or reaction body 5, for example, having a spherical shape. The diameter is preferably in the range of 2-10 mm. Particles 7a, 7b of an adsorption means and/or carrier bound enzymes are embedded in a base material 6 which is highly permeable and blood compatible. It is a special characteristic of the invention that, depending on the intended purpose one type of adsorption means or of a carrier bound enzyme may be used as well as any desired combination of such means. The grain size of the embedded particles may vary within a wide range and is preferably smaller than the entire diameter by the factor of 10-1000. The embedded particles may have any desired shape.

According to a further embodiment of the invention a possibility is provided to coat the adsorption or reaction body additionally in a manner known as such with an all around coating 8 in order to further increase its blood compatibility. In a special instance the coating 8 may be formed from the same substance as the base material 6 in order to make certain that the particles near the surface of the embedded material are positively prevented from coming into direct contact with the blood.

Following is a description of an example for the production of spherically shaped adsorption bodies comprising agarose forming the base material 6 and active charcoal or different adsorbent resins. This method may be used correspondingly without more in connection with other combinations of substances and it may be modified in different ways with which the person skilled in the art is familiar and suitable for the intended purpose.

EXAMPLE

For producing the base material agarose in powder form was used. Such agarose is produced among others by LKB Produkter, of Brommer, Sweden and Serva Feinbiochemika, of Heidelberg, Germany. Active charcoal in powder form as well as resins of the type Dowex 1×2, 1×4, 1×8 of different grain size as well as Amberlite XAD-2, XAD-4, and XAD-8 produced by Serva Feinbiochemika of Heidelberg, Germany were used as adsorbents. The resins were washed prior to their use several times in distilled water corresponding to twenty times the volume of the resins. The active charcoal was used without any pretreatment.

Three different suspensions were prepared of distilled water and 4% by weight, 6% by weight, and 8% by weight of powdered agarose and the suspension was heated on a water bath to 90° C. until the suspension was transformed into a liquid of uniform viscosity. Thereafter the adsorbents in the form of particles were admixed while carefully stirring in order to avoid the inclusion of air and to assure a uniform distribution of the particles in the agarose suspension. The quantity of adsorbents was preferably about 30% by weight.

The mixture was injected by means of a syringe, in a drop by drop manner, into a mixture of organic solvents kept at about 0° C. and comprising 1000 ml of toluol, 400 ml of chloroform, and 200 ml of hexane. The size of the spheres thus formed may be influenced within certain limits by varying the opening of the syringe and the injection speed. These spheres were dried after removal from the liquid baths for sometime, for example, thirty minutes, in air until a sufficient evaporation of the solvent whereupon the spheres were ready for use. Although the invention has been described with reference to specific example embodiments, it will be appreciated that it is intended to cover all modifications and equivalents within the scope of the appended claims.

We claim:

1. An apparatus for the detoxification of blood, comprising container means (1) having an inlet opening and an outlet opening, a plurality of reaction bodies (5) operatively held in said container means each of said reaction bodies having a given size, each of said reaction bodies comprising a blood compatible embedding material which is nonpermeable for corpuscular blood components and permeable to substances in solution to provide a molecular sieve, each of said reaction bodies having embedded therein active means in the form of a plurality of particles relatively smaller in size than said given size, said embedding material holding together said active particles in a substantially uniform distribution of the particle in the embedding material.

2. The apparatus of claim 1, wherein said active means comprise adsorption means.

3. The apparatus of claim 1, wherein said active means comprise enzyme means.

4. The apparatus of claim 1, wherein said reaction bodies further comprise outer surface layer means also made of said blood compatible, embedding material forming a molecular sieve.

5. The apparatus of claim 1, wherein said reaction bodies further comprise outer surface layer means made of a blood compatible material other than said first mentioned embedding material, said other material also being nonpermeable for corpuscular blood components but forming a molecular sieve.

6. The apparatus of claim 1, wherein said particles of said active means comprise carrier means and organic substances bound by said carrier means.

7. The apparatus of claim 1, wherein said active means comprise a mixture of different active components held in said embedding material of said reaction bodies.

8. The apparatus of claim 1, wherein said reaction bodies comprise different types of reaction bodies.

9. The apparatus of claim 8, wherein said different types of reaction bodies are arranged in a layer sequence in said housing means.

10. The apparatus of claim 1, wherein said reaction bodies have a substantially spherical shape.

11. The apparatus of claim 10, wherein said reaction bodies have different diameters.

12. The apparatus of claim 1, wherein said embedding material comprises agarose.

* * * * *

UNITED STATES PATENT AND TRADEMARK OFFICE
CERTIFICATE OF CORRECTION

PATENT NO. : 4,261,828
DATED : April 14, 1981
INVENTOR(S) : Gorig Brunner et al.

It is certified that error appears in the above—identified patent and that said Letters Patent is hereby corrected as shown below:

in [75] the inventor Gorig Brunner's address should read "Hannover" not --Hanover"; and the Assignee's name should read:

"Dr. Eduard Fresenius Chemisch-pharmazeutische Industrie KG. Apparatebau KG".

Signed and Sealed this

Seventh Day of July 1981

[SEAL]

Attest:

RENE D. TEGTMEYER

Attesting Officer     Acting Commissioner of Patents and Trademarks